(12) United States Patent
Messina et al.

(10) Patent No.: US 9,114,184 B2
(45) Date of Patent: Aug. 25, 2015

(54) DEVICE FOR THE HYGIENISATION OF MEDICAL INSTRUMENTS

(71) Applicant: EGOHEALTH S.r.l., Siena (IT)

(72) Inventors: Gabriele Messina, Siena (IT); Valerio Montagnani, Siena (IT); Sandra Burgassi, Siena (IT); Gabriele Cevenini, Siena (IT)

(73) Assignee: EgoHealth S.r.l., Siena (IT)

( * ) Notice: Subject to any disclaimer, the term of this patent is extended or adjusted under 35 U.S.C. 154(b) by 0 days.

(21) Appl. No.: 14/172,221

(22) Filed: Feb. 4, 2014

(65) Prior Publication Data

US 2014/0217307 A1 Aug. 7, 2014

(30) Foreign Application Priority Data

Feb. 5, 2013 (IT) .................................. MI13A0155

(51) Int. Cl.
*A61L 2/10* (2006.01)
*A61L 2/26* (2006.01)
*H01F 7/02* (2006.01)

(52) U.S. Cl.
CPC ... *A61L 2/10* (2013.01); *A61L 2/26* (2013.01); *A61L 2202/123* (2013.01); *A61L 2202/24* (2013.01); *H01F 7/0252* (2013.01)

(58) Field of Classification Search
CPC ............... A61L 2/10; A61L 2/26; A61L 2/24; A61L 2/0047; A61L 2202/122; A61L 2202/24; A61B 7/02; A61B 19/34; A61N 5/0624; A47L 13/17; A47L 13/51; H01F 7/0252

USPC ........... 250/455.11; 422/22, 24, 117; 181/131
See application file for complete search history.

(56) References Cited

U.S. PATENT DOCUMENTS

| | | | | |
|---|---|---|---|---|
| 4,867,268 A | * | 9/1989 | Ulert .............................. | 181/137 |
| 5,892,233 A | * | 4/1999 | Clement ................... | 250/455.11 |
| 6,340,350 B1 | * | 1/2002 | Simms .......................... | 600/528 |
| 6,461,568 B1 | * | 10/2002 | Eckhardt ......................... | 422/24 |
| 6,520,281 B1 | * | 2/2003 | Deslauriers et al. .......... | 181/131 |
| 7,189,983 B2 | * | 3/2007 | Aguirre et al. ............. | 250/504 R |
| 7,360,625 B2 | * | 4/2008 | Stickley ........................ | 181/131 |
| 7,560,706 B1 | * | 7/2009 | Castelluccio ............ | 250/455.11 |
| 7,705,325 B2 | * | 4/2010 | Vestal ...................... | 250/455.11 |
| 7,798,159 B2 | * | 9/2010 | Palfy et al. ..................... | 134/184 |
| 7,884,336 B2 | * | 2/2011 | Gibson .................... | 250/455.11 |
| 8,134,132 B2 | * | 3/2012 | Middlemass et al. .... | 250/455.11 |
| 8,203,124 B2 | * | 6/2012 | Havens et al. ........... | 250/455.11 |
| 8,318,090 B2 | * | 11/2012 | Gordon .......................... | 422/22 |
| 8,536,541 B2 | * | 9/2013 | Taylor et al. ............. | 250/455.11 |
| 2002/0119569 A1 | * | 8/2002 | Menz ........................... | 435/448 |
| 2002/0162972 A1 | * | 11/2002 | Pleet ........................... | 250/492.1 |
| 2002/0168287 A1 | * | 11/2002 | Eckhardt et al. ................ | 422/24 |
| 2003/0017073 A1 | * | 1/2003 | Eckhardt et al. ................ | 422/24 |
| 2004/0114767 A1 | * | 6/2004 | Tseng ............................. | 381/67 |

(Continued)

*Primary Examiner* — Jack Berman
*Assistant Examiner* — Wyatt Stoffa
(74) *Attorney, Agent, or Firm* — Dickstein Shapiro LLP

(57) ABSTRACT

The present invention relates to a device for the hygienization of medical instruments, in particular stethoscopes.
In particular, the present invention relates to a hygienization or sterilization system (1) of a medical-healthcare instrument, comprising a hygienization or sterilization device (2) and a coupling member (3) associable to said medical-healthcare instrument, characterized in that the coupling between said coupling member (3) and said device (2) is actuated by magnetic coupling means.

22 Claims, 4 Drawing Sheets

(56) References Cited

U.S. PATENT DOCUMENTS

| | | | |
|---|---|---|---|
| 2005/0112021 A1* | 5/2005 | Hlavinka et al. | 422/24 |
| 2005/0254992 A1* | 11/2005 | Jenkins et al. | 422/24 |
| 2005/0269216 A1* | 12/2005 | Ovadia | 206/6.1 |
| 2006/0147339 A1* | 7/2006 | Hunter et al. | 422/24 |
| 2009/0014232 A1* | 1/2009 | Hirsch et al. | 181/131 |
| 2009/0026237 A1* | 1/2009 | Weaver | 224/269 |
| 2009/0189084 A1* | 7/2009 | Pinsky | 250/455.11 |
| 2009/0212234 A1* | 8/2009 | Vestal | 250/455.11 |
| 2009/0218512 A1* | 9/2009 | Ranta et al. | 250/455.11 |
| 2009/0290719 A1* | 11/2009 | Kugler et al. | 381/67 |
| 2010/0044582 A1* | 2/2010 | Cooper et al. | 250/455.11 |
| 2011/0126370 A1* | 6/2011 | Reuben | 15/167.1 |
| 2011/0172810 A1* | 7/2011 | Mlodzinski et al. | 700/230 |
| 2011/0209442 A1* | 9/2011 | Freeman et al. | 53/425 |
| 2011/0215054 A1* | 9/2011 | Lantis et al. | 210/748.1 |
| 2012/0051969 A1* | 3/2012 | Nahman et al. | 422/28 |
| 2012/0261593 A1* | 10/2012 | Noori | 250/492.1 |
| 2013/0056425 A1* | 3/2013 | Lantis et al. | 210/748.11 |
| 2013/0063922 A1* | 3/2013 | La Porte et al. | 361/807 |
| 2013/0150729 A1* | 6/2013 | Zuluage | 600/476 |

* cited by examiner

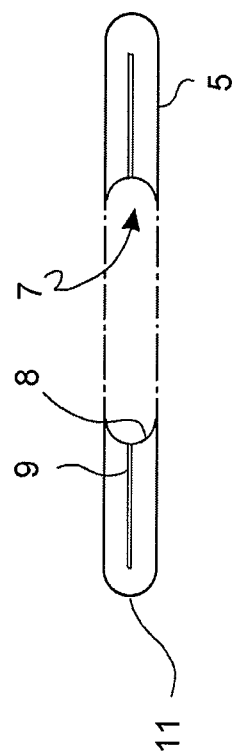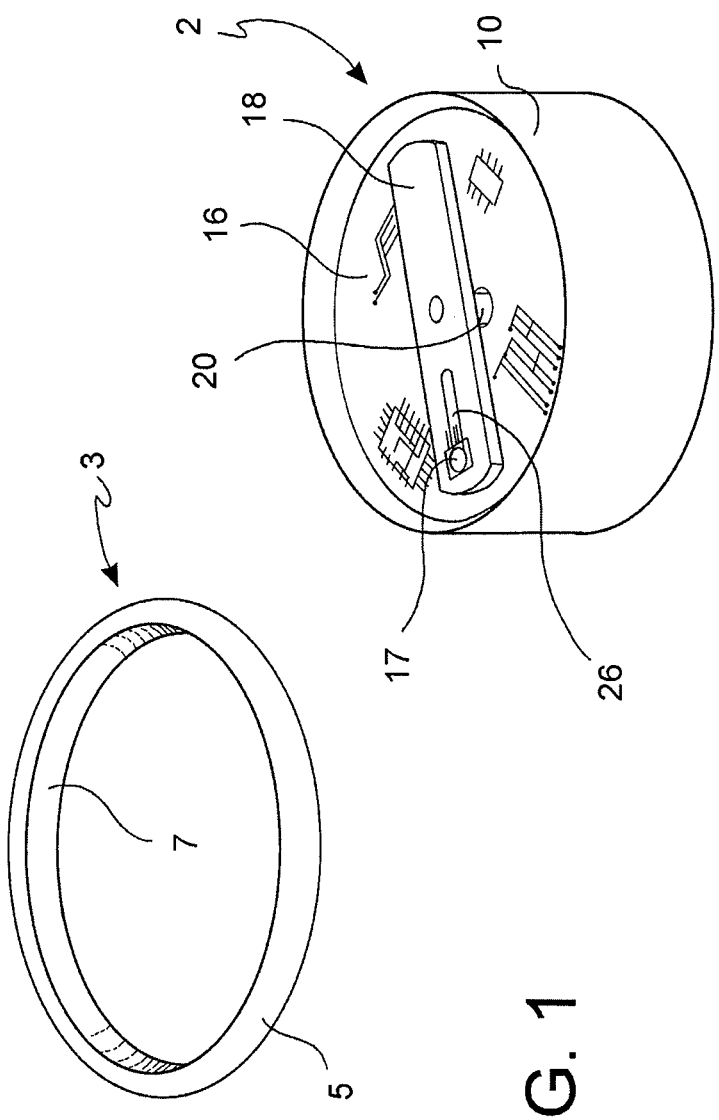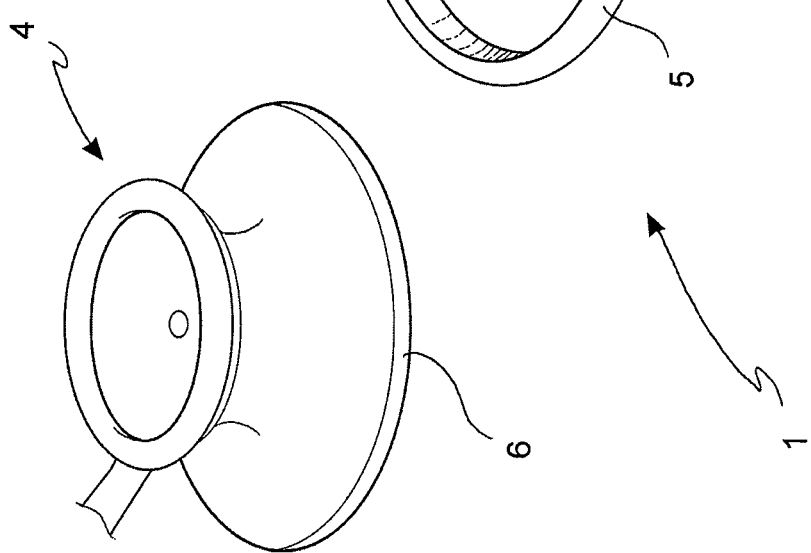

DEVICE FOR THE HYGIENISATION OF MEDICAL INSTRUMENTS

FIELD OF THE INVENTION

The present invention relates to a device for the hygienisation OR sterilisation of medical instruments, in particular stethoscopes.

BACKGROUND ART

In clinical and outpatient practice, doctors and health operators make wide use of portable instruments, frequently used both to evaluate the main physiological conditions of the patient and for treatment purposes, as also to communicate or register clinical data.

The hygiene of such instruments is of fundamental importance in that it is known how a lack of sterility thereof often entails serious health risks. In fact, a significant percentage of infective disease is of iatrogenic origin, linked mainly to a lack of hygiene. Such diseases, as well as obviously impairing the health of the patient, significantly increase clinical and health costs.

The majority of portable instruments are disposable and as such, are suitably closed in sealed sterile packaging; these comprise needles, syringes, gauzes, electrodes etc.

Other instruments, generally more expensive, used by health care personnel, such as forceps, clamps, surgical instruments, catheters etc. are sterilised before use each time in special machinery, generally considerably expensive, cumbersome and sophisticated, located in specific areas quite separate from the operating theatres.

There are however various instruments used by healthcare operators (primarily doctors), such as stethoscopes, thermometers, manometers, otolaryngological retractors, ophthalmic frames and lenses, etc. the hygienisation of which must necessarily be performed frequently and repeatedly, whenever use is required in different subjects.

Unfortunately, despite the problem of cross infection (from doctor to patient and from patient to patient through non-disposable medical instruments) being widely known, evident and ascertained at a scientific level, and there being a wide perception of the elevated efficacy of meticulous hygienisation of such instruments to prevent hospital infections, little attention is paid by doctors and healthcare operators to performing systematic hygienisation of the instruments between one patient and the next. This is often due to practical reasons and the priority of medical treatment which focuses mainly on treating the patient and restoring his vital functions.

Among the frequently and repeatedly used instruments, and thus a possible vehicle of infection, the stethoscope is the most common, with a high risk of transmission of iatrogenic infections. The function of the stethoscope, by means of contact of the head thereof with various parts of the patient, is to detect the sounds of the patient's organs and interpret them so as to determine the physiological or pathological conditions thereof.

There is wide evidence in the literature that stethoscopes may be a vehicle of cross infection from one patient to another. In fact, it is rare, albeit desirable, for a doctor to disinfect a stethoscope after each examination.

A fundamental role in the lack of attention to hygienisation is the practical difficulty of adequate hygienisation/sterilisation in the normal operating conditions of the doctor. The stethoscope is, in fact, an instrument which a doctor generally brings with him during his visits, often itinerant, while, as said, sterilisation devices are normally cumbersome and housed in dedicated rooms. Consequently, even in the case in which disinfecting were carried out by the doctor after each examination, it would, more often than not, be hurried, inadequate and in any case uncontrolled as regards efficacy and safety.

Hygienisation systems which are simple, lightweight, compact, portable, safe and reliable both in safeguarding healthcare operators and patients, and in the efficacy of their action, are therefore desirable.

To hygienise or sterilise medical-healthcare instruments either chemical substances, or approaches based on physical mediums may be used. The latter, compared to the former, do not suffer from microbial resistance nor do they generate it in that they do not use selection mechanisms but are generally associated with cumbersome and expensive devices and are thus typically intended for hospital use.

Among the effective and tested physical systems is the one using UV rays. It has been demonstrated that UV rays have a safe disinfectant property (lowering of the microbial content), especially in the range of wavelengths between 255 and 280 nm, with a sterilising effect (elimination of the microbial content) when exposure time is sufficiently prolonged.

Hygienisation devices have been proposed which function on the UV ray principle. However, on account of the space they occupy, the inconvenience of use, complexity and elevated cost, they do not configure as a real solution to the problem highlighted above.

One important parameter in the design of a device of this type is the safety of the operator and the patient, in particular to avoid skin and eye damage caused by UV rays. This problem too has not been resolved by the devices of the prior art in a practical and economical way.

SUMMARY OF THE INVENTION

The purpose of the present invention is to make available a device for the hygienisation or sterilisation of medical-healthcare instruments, in particular stethoscopes which overcomes the above problems and which thus: has a light weight and limited dimensions such as to make it practically portable; is simple, effective and safe to use; enables operator-free automatic hygienisation or sterilisation in sufficiently short times to enable the operator to repeat it after each use.

Such purpose is achieved by a device for the hygienisation or sterilisation of medical-healthcare instruments as delineated in the appended claims, the definitions of which form an integral part of this description.

Further characteristics and advantages of the present invention will, in any case, be evident from the description given below of some embodiments, made by way of a non-limiting example.

BRIEF DESCRIPTION OF THE DRAWINGS

FIG. 1 shows an exploded, perspective view of the stethoscope set, coupling member and hygienisation device according to the invention;

FIG. 2 shows a side view in cross-section of the coupling member in FIG. 1;

DETAILED DESCRIPTION OF THE INVENTION

Figure 3:
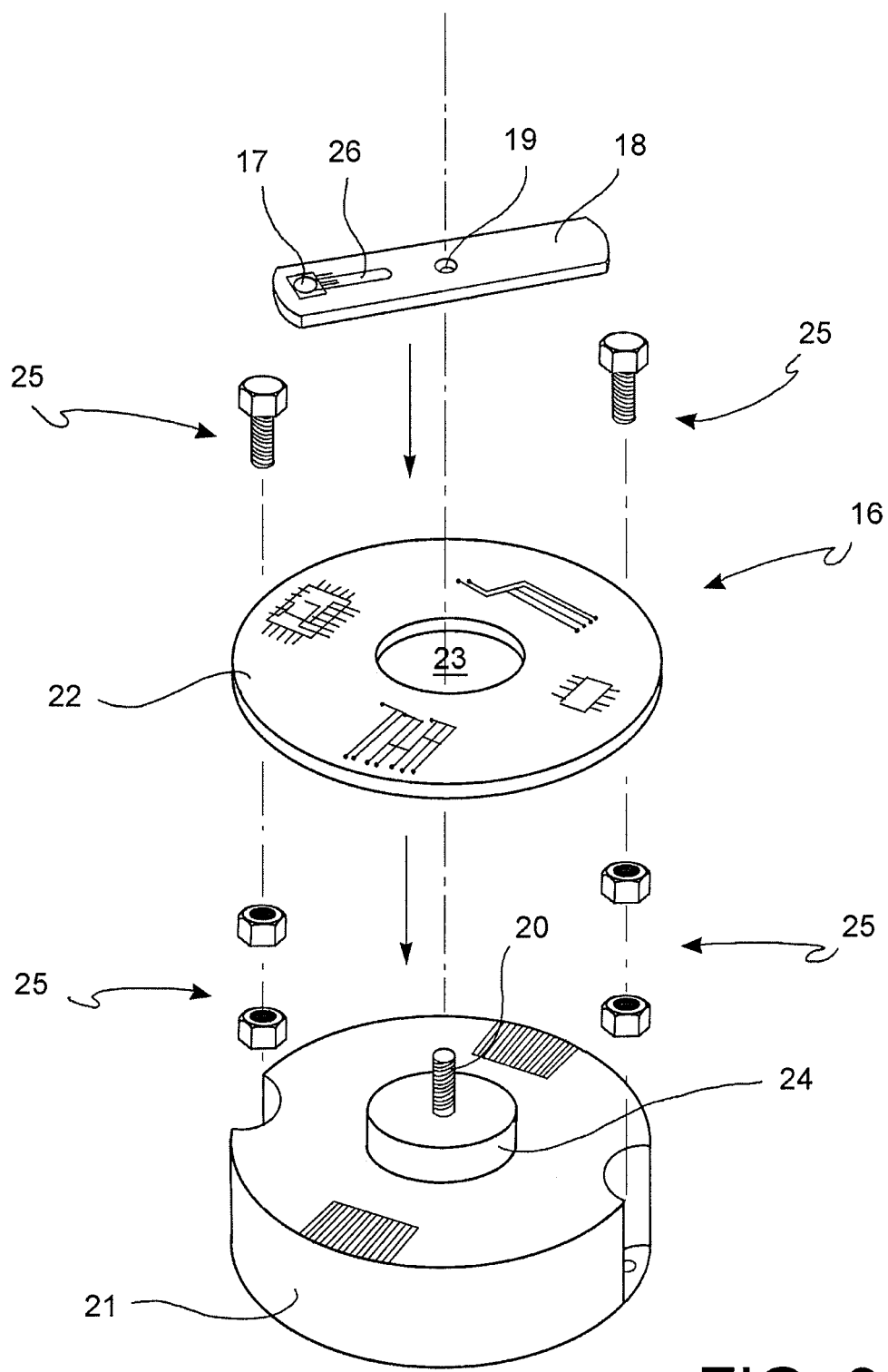
FIG. 3 shows an exploded, perspective view of the hygienisation device according to the invention.

The term "medical-healthcare instrument" indicates a non-disposable instrument having a surface destined to come into contact with the body of a person, both for medical-healthcare reasons, as happens with the instruments normally used by doctors and nurses, or for personal reasons, such as for examples babies' dummies or other objects used for infants.

With reference to the figures, reference numeral 1 globally denotes the hygienisation or sterilisation system according to the invention which comprises a hygienisation or sterilisation device 2 and a coupling member 3 to a medical-healthcare instrument, in the case in point a stethoscope 4.

The coupling member 3, a cross-section of which is shown in FIG. 2, comprises an elastic ring 5, coupling to the rim 6 of the head of the stethoscope 4, and adaptable, thanks to the elasticity of the material, to the various dimensions and shapes (circular, elliptical, etc.) of the stethoscope. The elastic ring 5 is typically made of rubber or a synthetic elastomer.

The elastic ring has a C-shaped profile 8 along the inner rim 7 so as to be able to grip the rim 6 of the stethoscope and remain firmly coupled thereto thanks in part to the elastic force of the material.

A metal sheet 9 is joined to the elastic ring 5, which metal sheet may be embedded in the body of the elastic ring or applied externally. The metal foil 9 is made in a ferromagnetic material, so as to be couplable to a magnet.

The outer rim 11 of the elastic ring 5 may have a differently shape profile. In fact, as well as the rounded profile shown in FIG. 2, it may have the flared profile shown in FIG. 4. In such case, a shaped coupling between the elastic ring 5 and device 2 may be realised. However, in order to be able to better adapt the device 2 to any type of stethoscope, it will be preferable for the coupling between the elastic ring 5 and device 2 to take place merely by juxtaposition and for the elastic ring 5 to have a sufficiently ample surface to always create a physical contact with the rim of the device 2 even when the ring 5 is deformed to adapt to the various shapes and sizes of stethoscope.

The hygienisation or sterilisation device 2 comprises a case 10, typically a cylindrical shape, having a bottom 12 and side walls 13. The case 10 is open on the side opposite the bottom 12 and has a coupling edge 14 with the coupling member 3 and thus with the stethoscope 4.

Magnetic coupling means 15 are associated to the coupling edge 14, for example in the form of a continuous or interrupted ring. The magnetic coupling means 15 are typically a permanent magnet, even though in other embodiments an electromagnet may be provided for.

Hygienisation or sterilisation means 16 are housed inside the case 10. Preferably, the hygienisation or sterilisation means 16 comprise UV radiation emission means. Preferably, said means comprise a UV LED 17 which emits a radiation with wavelength ranging between 255 and 280 nm, preferably approximately 260 nm.

The UV radiation emission means face towards the open side of the case 10, so as to irradiate the surface of the head of the stethoscope 4 to be hygienised when the device 2 is coupled thereto.

In a preferred embodiment, the hygienisation or sterilisation means 16 are mobile. This way, the irradiation of the entire surface of the head of the stethoscope is obtained using a single UV LED 17.

Figure 4:
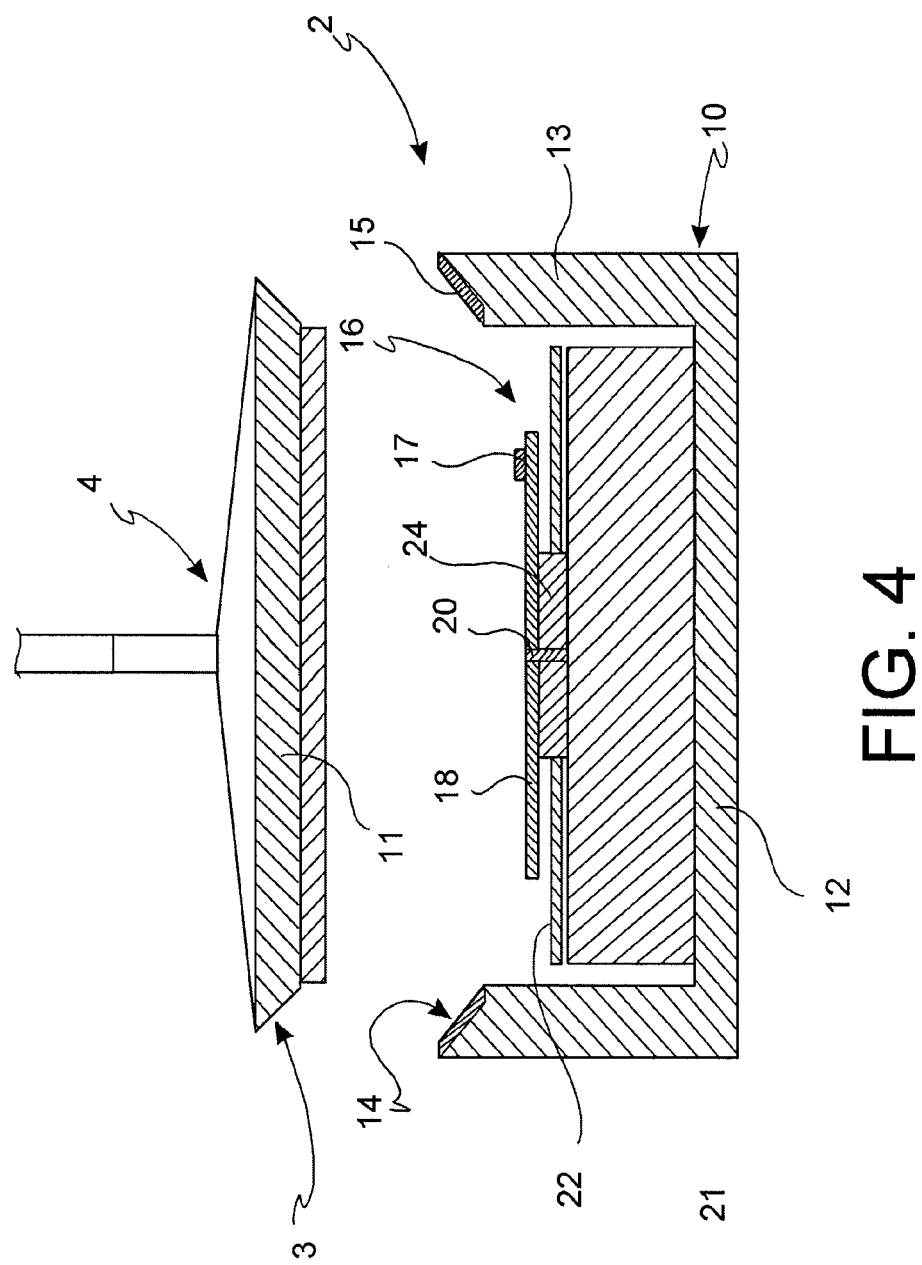
FIG. 4 shows a side view in cross-section of the stethoscope set—hygienisation device according to the invention.

As shown in FIGS. 3 and 4, in a preferred embodiment, the hygienisation or sterilization means 16 comprise a rotating member 18, on which the UV LED 17 is positioned.

In different embodiments, the rotating member 18 may have different geometric shapes and dimensions. In particular, it may go as far as to cover the entire surface of the drive and control unit 22. In certain embodiments the rotating member 18 may have a polyhedral surface, the geometry of which is designed so as to diffuse the UV rays over various points.

The rotating member 18 has a central hole 19 which is attached to the shaft 20 of a motor 21, so as to rotate integrally therewith. Preferably, a stepper motor is used. The UV LED 17 will have a broad angle of illumination so as to require only two or three steps of the motor 21, which is appropriately miniaturised to reduce the weight and dimensions thereof.

A battery is associated to the motor 21, preferably a lithium battery, rechargeable both by connection to the grid, for example by means of a cable with micro/mini USB connector, or in wireless mode by electromagnetic induction. This assures the maximum portability of the device.

In some embodiments the motor, the battery and the control electronics could be placed externally to the housing 10.

In certain embodiments, the motor 21 is electrically connected to the UV LED 17 and comprises a switch to start or stop the rotation of the rotary member 18 and to turn the UV LED on or off. The same manual command may be used to activate or deactivate both functions, or separate switches may be provided.

In a preferred embodiment, the hygienisation or sterilization means 16 comprise a drive and control unit 22 comprising a microprocessor or a micro controller, optionally with Digital Signal Processing—DSP functions.

In the embodiment in FIG. 3, the drive and control unit 22 comprises a central hole 23 so as to position itself sandwiched between the motor 21 and the rotating member 18. For example, the motor 21 comprises a cylindrical central prominence 24 which the shaft 20 comes out of, having a diameter corresponding to that of the hole 23 of the drive and control unit 22, so as to stably house it. Suitable electrical contacts connect the drive and control unit 22 to the motor 21 and to the UV LED 17. Considering that the drive and control unit 22 is fixed, as is the body of the motor 21, while the rotating member 18 which the UV LED 17 is positioned on is mobile, such electrical contacts comprise sliding contacts or appropriate wiring specifically provided for such configuration. For example, the shaft 20 and the rotating member 18 may comprise a metal track which slides on an annular contact present on the central cylindrical prominence 24, in turn in contact with the drive and control unit 22.

Appropriate attachment means 25, such as for example a screw-nut system, attach the drive and control unit 22 to the motor 21 and the latter to the case 10.

Figure 6:
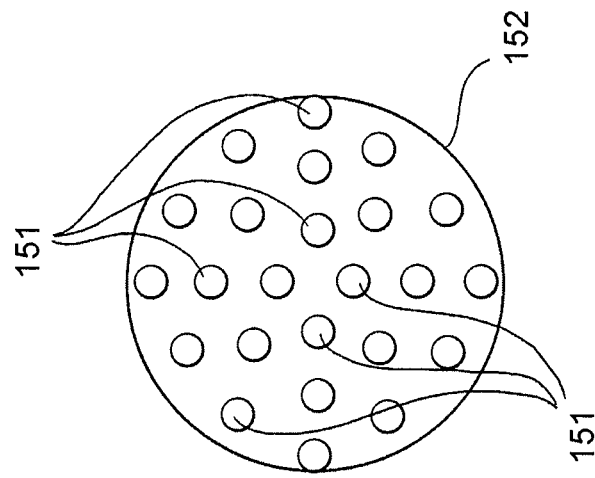
FIG. 6 shows a plan view of a detail of the embodiment in FIG. 5.
Figure 5:
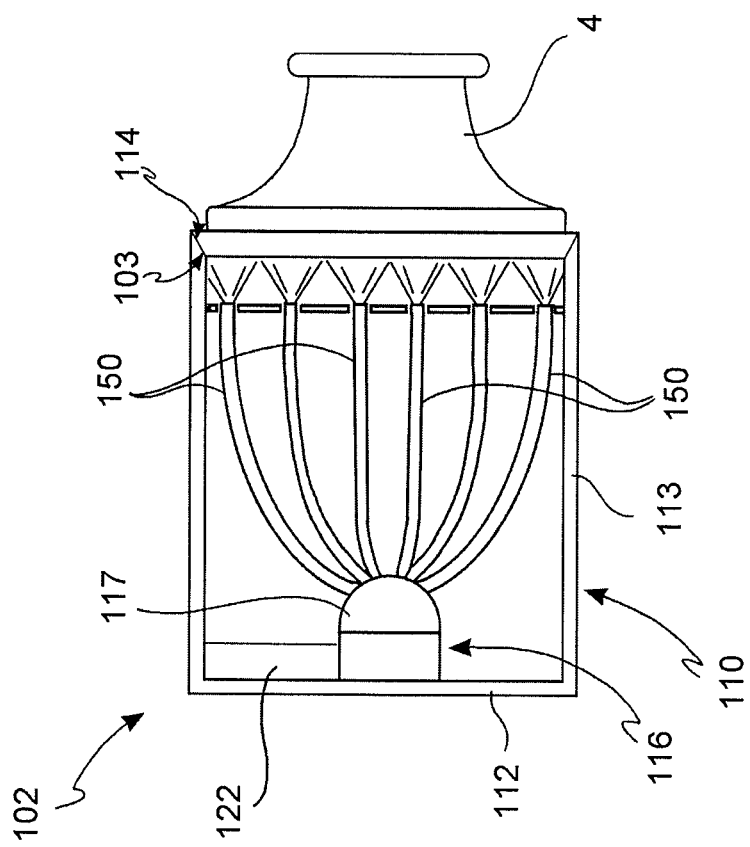
FIG. 5 shows a schematic side view in cross-section of a different embodiment of the hygienisation device according to the invention.

In a different embodiment, shown in FIGS. 5 and 6, wherein the motor is not present, the irradiation of the entire surface of the membrane of the stethoscope—or of other biomedical instruments—is ensured by the use of a single UV LED combined with lighting systems based on optic conduction wherein the light is transported to the surface to be sterilised by means of ducts, tubes, guides and optic fibres in glass, quartz, techno polymers or gels, suitable to transport UV rays without jeopardising the disinfectant power thereof.

The device 102 in FIG. 5 comprises a case 110 having a bottom 112 and side walls 113, the case 110 being open on the side opposite the bottom 112 and presenting a coupling edge 114 with the coupling member 103. Magnetic coupling means (not shown) are associated to the coupling edge 114, entirely analogous to the previous embodiment.

Hygienisation or sterilisation means 116 which comprise UV radiation emission means, for example a UV LED 117 are placed on the bottom 112. A bundle of optic fibres 150 or other conduction means of the UV radiation leave from the UV LED 117.

A plate 152 provided with a plurality of holes 151 is positioned next to the open side of the case 110, in such a way that the holes 151 face the membrane of the stethoscope 4 when it is associated to the device 102 by means of the coupling member 103.

The UV radiation conductors or optic fibres 150 terminate at the holes 151 of the plate 152 so as to evenly illuminate the surface to be hygienised.

The number of optic fibres 150 or of UV conductors and holes 151 of the plate 152 will be such as to permit as even a distribution as possible of the UV radiation over the surface to be hygienised.

In other embodiments, instead, a plurality of fixed LEDs may be placed on the bottom 112 of the case 110.

The device also comprises a drive and control unit 122 comprising a microprocessor or a micro controller also having Digital Signal Processing—DSP functions.

The drive and control unit 22, 122 performs the following functions a) control of the closure of the device 2 on the head of the stethoscope 4 and forwarding of an enabling command to carry out steps b) and c);

b) driving and control of the turning on/off of the motor 21 and of the speed of rotation of the shaft 20, where present;

c) driving and control of the turning on/off of the UV LED 17 based on pre-set turning on times and power supplied;

d) control of anomalies, such as malfunctioning of the UV LED 17, insufficient lighting power on the surface to be disinfected and exhausted battery charge.

In the embodiment in FIG. 5, the drive and control unit 122 perform its functions on the UV LED 117, in the aforesaid steps a), c) and d).

Such operations are performed using conventional logic elements widely known to the expert in the sector.

In the embodiment comprising a motor 21, steps b) and c) may be inverted, but it is essential for step a) to be performed first so as to send the microprocessor an enabling command for steps b) and c).

Step d) may be performed at any moment,

The checking of closure in step a) is important to ensure the safety of the operator. In fact, were the UV LED 17, 117 to start functioning before the closure of the device, the UV radiation could endanger the health of the operator, especially if it were to reach the eyes or other sensitive body parts.

In certain embodiments, the control of step a) is implemented by a contact or magnetic induction switch which provides for the closure or opening of the electric circuit depending on whether the device 2 is respectively coupled or uncoupled to the elastic ring 5. Alternatively, the elastic ring 5 may provide for suitable electric contacts for closing the circuit. For example, the positioning of the metal foil 9 could be provided for externally or at least it could be made to surface in one or more points to establish an electric contact.

In certain embodiments, in addition to or in place of the contact switch described above, the means 16, 116 provide for a visible light sensor (not shown) connected to the drive and control unit 22, 122 to send a turning on command only in the case in which no visible light is detected within the case 10, 110. This would in fact mean that the closure of the device 2 on the stethoscope 4 had not been properly performed.

In certain embodiments, the hygienisation or sterilization means 16 comprise a proximity sensor (not shown) which detects the distance between the UV LED 17 and the surface of the stethoscope 4 to be hygienised, and sends a control signal to the drive and control unit 22 to vary such distance in the case of a deviation from a preset value. In this embodiment, such distance may be adjusted by making the rotating member 18 slide along the shaft 20 of the motor 21 in a manual, driven or automated manner.

In certain embodiments, the inner surface of the device 2, in particular that of the case 10, 110 is reflective. For example, a foil or gold or silver plating may be provided.

In certain embodiments the case 10, 110 may also have a polyhedral surface, the geometry of which is designed so as to diffuse the UV rays over various points.

This way, the efficacy of the treatment is increased, in that the UV radiation will be efficiently channeled towards the surface to be hygienised.

In certain embodiments, the UV LED 17 is radially mobile on the rotating member 18. To such purpose a skate 26, as shown in FIGS. 1 and 3, may be provided. The adjustment may be manual, driven or automatic. It is in fact important for the UV LED to be appropriately positioned in relation to the surface to be hygienised so as to irradiate it evenly. Considering that the dimensions of stethoscopes may be different, such adjustment makes it possible to ensure optimal hygienisation in all cases.

In certain embodiments, the rotating member 18 may house two or more LEDS, so as to make the hygienisation or sterilisation faster.

The hygienisation or sterilisation device 2 is pocket-sized. In certain embodiments, the device 2 comprises anchoring means (not shown) such as for example a clip, spring clip, hook or ring which a small chain is made to pass through, so as to prove portable and exposed externally, by means of connection to the operator's clothing, or by hanging it from his neck.

The hygienisation or sterilisation device 2 may come with a protective container in an electrically insulating, polymer material, opaque and resistant to UV rays (not shown). The protective container may be used when the device 2 is not in use.

In general, the device 2 and its protective container are made of a material resistant to UV irradiation, so as not to be damaged or deteriorated after being used only several times, or possibly improperly by the operator.

The functioning of the device 2 according to the invention is clear from the above description. The medical-healthcare operator, once completed the examination, may couple the head of the stethoscope 4 to the device 2 simply and immediately thanks to the magnetic coupling. At this point, either manually or automatically the hygienisation/sterilisation cycle will be started, at the end of which the operator may uncouple the device 2 from the stethoscope, which is now ready to be used again.

In certain embodiments, the device 2 may emit an acoustic, luminous or vibration signal to signal completion of the hygienisation/sterilisation cycle.

The charging of the battery may, as said, be performed in wireless mode or by connection to the grid. In certain embodiments, the drive and control unit 22, 122 may adjust the power dispensed by the UV LED 17, 117, dispensing a greater power if the device is connected to the grid, for example while recharging the battery, so as to hygienise or sterilise the medical device completely. This way hygienisation or sterilisation during the non-operative step is guaranteed and at the same time the duration of the battery is prolonged.

The system 1 is made in a modular manner as regards its components so that it can be structured in the various forms described, merely by removing or adding components having different functions (modules).

The system 1 is made so as to act as a module of a broader and more complex system wherein measurement modules, modules for transducing, conditioning, converting, memorising, processing, transmitting and receiving biomedical analogue and digital signals and data are easily connectable to each other, or suitable for integrating and/or inserting inside the device itself.

The advantages of the hygienisation or sterilisation device 2 according to the invention are evident.

The device has a minimal weight and dimensions and is portable.

Despite being suitable for coupling and uncoupling from the stethoscope in a single move, thanks to the magnetic coupling means, it may however be entirely separated from the stethoscope, thereby both preventing its contamination during the use of the stethoscope on a patient, and preventing it from getting in the operator's way.

The use of the UV LED 17 permits a miniaturisation of the device; the provision of the rotating member 18, together with the case 10, with reflective and possibly polyhedral surfaces, or, combined with or instead, the use of optic ducts, ensures a complete and effective irradiation of the entire surface to be hygienised in a short time, perfectly compatible with the time between examining one patient and the next, even using only one LED. Considering that the latter is the greatest cost element of the device, the possibility of using only one LED to cover the entire surface ensures a substantial containment of production costs as well as a longer duration of the battery.

The drive and control unit 22, 122 makes it possible to perform all the operations in an entirely automatic manner, at the same time making it safe for the operator—the functioning of the LED is inhibited if the device is not perfectly closed onto the stethoscope or is opened before termination of the hygienisation or sterilisation operations—and for the patient—the duration and intensity of the sterilisation cycle is regulated by the microprocessor or micro controller—.

It is evident that only some particular embodiments of the present invention have been described, to which a person skilled in the art may make those modifications required for its adaptation to specific applications, while remaining within the scope of protection as defined in the appended claims.

In particular, in the case in which the device is applicable to instruments other than a stethoscope, the shape of the coupling member and of the case 10 of the device will need to be modified so as to adapt to the specific structural characteristics of the instrument.

The modular design of both the inner components and of the device itself, makes it possible to pass from one embodiment to another in an extremely simple manner and to change its structural configuration while maintaining its function and integrating it perfectly in measurement, control and processing systems of biomedical signals.

What we claim is:

1. A system for disinfecting a head of a stethoscope, comprising:
    a disinfectant device including a case and an opening defined by a rim, a UV radiation source located in the case and emitting UV radiation towards the opening, the disinfectant device including a source of magnetism which generates a magnetic field in the area of the rim; and
    an elastic ring having an inner opening and a mating surface adapted to mate with the rim of the opening in the disinfectant device, the elastic ring having ferromagnetic characteristics, the shape of the inner opening and the elasticity of the elastic ring allowing it to be placed over and removed from stethoscope heads of various configurations, such that when the elastic ring is placed over a stethoscope head, the mating surface of the elastic ring can be placed in mating contact with the rim of the opening in the disinfectant device and the elastic ring, and with it the stethoscope head, will be held on the rim by the magnetic field generated by the source of magnetism with the stethoscope head facing the source of UV radiation.

2. The system of claim 1, wherein the source of magnetism is one or more permanent magnets located on the rim.

3. The system of claim 1, wherein the rim is in the form of a conical frustum.

4. The system of claim 3, wherein the portion of the elastic ring having a shape to mate with the rim of the disinfectant device is also in the form of a conical frustum.

5. The system of claim 1, wherein the elastic ring is embedded with a ferromagnetic metal.

6. The system of claim 5, wherein the metal comprises a ferromagnetic metal sheet.

7. The system of claim 1, wherein the ferromagnetic characteristics of the elastic ring are provided by ferromagnetic metal located on an outer surface of the elastic ring.

8. The system of claim 1, wherein elastic ring has an inner surface which allows it to elastically and removably hold the head of the stethoscope the inner surface having a c-shaped profile.

9. The system of claim 1, wherein the elastic ring forms a light tight fit with the rim when it is placed in the opening and is held on to the rim by the magnetic field.

10. The system of claim 1, wherein the UV radiation source comprises at least one UV LED emitting a radiation having a wavelength between 255 and 280 nm.

11. The system of claim 10, wherein the at least one UV LED is mounted on a rotating member and further including a motor for rotating the rotating member, and with it the at least one UV LED, about an axis of the motor.

12. The system of claim 11, wherein the disinfectant device further includes a microprocessor or microcontroller for controlling the operation of the UV source and the motor.

13. The system of claim 12, wherein the microprocessor controls the rotational speed of the motor.

14. The system of claim 12, wherein the microprocessor shuts off the at least one UV LED after the rotating device has been rotated a predetermined number of times around the axis of the motor.

15. The system of claim 12, further including a sensor, electronically coupled to the microprocessor or microcontroller and which detects the fact that the elastic ring has been placed in the opening and mated with the rim, and wherein the microprocessor or microcontroller turns on the UV LED and the motor in response to the fact that the sensor has sensed that the elastic ring has been placed in the opening and mated with the rim.

16. The system of claim 15, wherein the sensor comprises a contact sensor or a magnetic induction switch.

17. The system of claim 15, wherein the sensor is a visible light sensor.

18. The system of claim 15, wherein the microprocessor adjusts the amount of UV radiation applied to the stethoscope head when the head of the stethoscope is grasped by the elastic ring and the elastic ring is placed in the opening adjacent the rim.

19. The system of claim 15, wherein the at least one UV LED is on an adjustable shaft which allows the distance between the at least one UV LED and the opening to be adjusted and the microprocessor or microcontroller controls the distance by controlling the adjustable shaft.

20. The system of claim 12, wherein at least one of the UV LEDs are movable radially along the rotating member.

21. The system of claim 1, further including a plate having a plurality of holes facing the opening, and wherein the UV radiation source is a single UV LED which supplies UV radiation to the holes so as to irradiate the stethoscope head with UV radiation when the head of the stethoscope is grasped by the elastic ring and the elastic ring is placed in the opening adjacent the rim.

22. The system of claim 21, wherein a plurality of optical fibers guide UV radiation emitted by the UV radiation source to the holes.

* * * * *